US011154226B2

(12) United States Patent
Tai et al.

(10) Patent No.: US 11,154,226 B2
(45) Date of Patent: Oct. 26, 2021

(54) MEDICAL SENSOR HAVING A NANOSCALE TAPERED WAVEGUIDE FOR SPECTROSCOPY-BASED ANALYSIS OF FLUID

(71) Applicants: California Institute of Technology, Pasadena, CA (US); University of Southern California, Los Angeles, CA (US)

(72) Inventors: Yu-Chong Tai, Pasadena, CA (US); Hyuck Choo, San Marino, CA (US); Ramiro Magalhaes Ribeiro, South Pasadena, CA (US); Mark S. Humayun, Glendale, CA (US)

(73) Assignees: California Institute of Technology, Pasadena, CA (US); University of Southern California, Los Angeles, CA (US); Doheny Eye institute, Los Angeles, CA (US)

( * ) Notice: Subject to any disclaimer, the term of this patent is extended or adjusted under 35 U.S.C. 154(b) by 1000 days.

(21) Appl. No.: 15/179,744

(22) Filed: Jun. 10, 2016

(65) Prior Publication Data

US 2016/0361001 A1 Dec. 15, 2016

Related U.S. Application Data

(60) Provisional application No. 62/175,078, filed on Jun. 12, 2015, provisional application No. 62/201,383, filed on Aug. 5, 2015.

(51) Int. Cl.
*A61B 5/00* (2006.01)
*A61B 5/145* (2006.01)
(Continued)

(52) U.S. Cl.
CPC ........ *A61B 5/1459* (2013.01); *A61B 5/14532* (2013.01); *A61B 5/14539* (2013.01);
(Continued)

(58) Field of Classification Search
CPC ..... A61B 5/7246; A61B 5/742; A61B 5/0075; A61B 5/1455; A61B 5/14551;
(Continued)

(56) References Cited

U.S. PATENT DOCUMENTS

| 2002/0126953 | A1* | 9/2002 | Wach | ................. | G02B 6/12007 |
| | | | | | 385/24 |
| 2003/0174992 | A1* | 9/2003 | Levene | ............. | G01N 21/6452 |
| | | | | | 385/129 |

(Continued)

OTHER PUBLICATIONS

Hyuck Choo, Nanofocusing in a metal-insulator-metal gap plasmon waveguide with a three-dimensional linear taper, Nov. 18, 2012, Nature Photonics, pp. 1-7 (Year: 2012).*

(Continued)

*Primary Examiner* — Chu Chuan Liu
(74) *Attorney, Agent, or Firm* — Kilpatrick Townsend & Stockton LLP (57) ABSTRACT

A medical sensor is described. In an example, the medical sensor includes a nanoscale tapered waveguide attached to a substrate. The nanoscale tapered waveguide includes a nanoscale channel that receives fluid and an excitation light and that outputs a response light. The excitation light propagates through the fluid. A receiving channel of the nanoscale channel is configured as a waveguide that receives and guides the excitation to a linearly tapered channel of the nanoscale channel. The linearly tapered channel has three dimensional linear tapering that focuses the excitation light guided from the receiving channel into an optical response channel of the nanoscale channel. In turn, the optical response channel is configured as a waveguide that outputs
(Continued)

a response light in response to the excitation light focused from the linearly tapered channel. The response light corresponds to a response of an analyte of the fluid present in the optical response channel.

23 Claims, 7 Drawing Sheets (51) Int. Cl.
```
A61B 5/1459      (2006.01)
G02B 6/10        (2006.01)
G02B 6/122       (2006.01)
G01J 3/44        (2006.01)
G01N 21/65       (2006.01)
G02B 6/34        (2006.01)
G01N 21/64       (2006.01)
G02B 6/12        (2006.01)
```
(52) U.S. Cl.
CPC ........ *A61B 5/14546* (2013.01); *A61B 5/7246* (2013.01); *A61B 5/7282* (2013.01); *A61B 5/742* (2013.01); *A61B 5/7475* (2013.01); *G01J 3/44* (2013.01); *G01J 3/4406* (2013.01); *G01N 21/65* (2013.01); *G02B 6/107* (2013.01); *G02B 6/1228* (2013.01); *G01N 21/64* (2013.01); *G01N 2021/653* (2013.01); *G02B 6/34* (2013.01); *G02B 2006/12107* (2013.01)

(58) Field of Classification Search
CPC ............ A61B 5/14532; A61B 5/14546; A61B 5/14539; A61B 5/7475; A61B 5/1459; A61B 5/7278; A61B 2562/0233; B02B 6/34; B02B 6/107; B02B 6/1228
See application file for complete search history.

(56) References Cited

U.S. PATENT DOCUMENTS

| | | | | |
|---|---|---|---|---|
| 2012/0226118 | A1* | 9/2012 | Delbeke | A61B 5/0031 600/316 |
| 2014/0277291 | A1* | 9/2014 | Pugh | G02C 7/04 607/88 |
| 2014/0363127 | A1* | 12/2014 | Baets | G02B 6/124 385/37 |
| 2015/0202456 | A1* | 7/2015 | Andersen | A61N 1/0551 604/20 |
| 2016/0067357 | A1* | 3/2016 | Francois | C12Q 1/37 424/9.6 |

OTHER PUBLICATIONS

T. M. Hard, Laser Wavelength Selection and Output Coupling by a Grating, Aug. 1970, Applied Optics, Bol. 9, No. 8, pp. 1825-1830 (Year: 1970).*
Matthew White Royal, Droplet-Based Sensing: Optical Microresonator Sensors Embedded in Digital Electrowetting Microfluidics Systems, Dec. 2013, IEEE Sensors Journal, vol. 13, No. 12, pp. 4733-4742 (Year: 2013).*
W. L. Barnes, A. Dereux, T. W. Ebbesen, Surface plasmon subwavelength optics, Nature, Aug. 14, 2003, p. 824-830, vol. 424.
S. Borkar, A. A. Chien, The future of microprocessors, Communications of the ACM, May 2011, p. 66-77, vol. 54, No. 5.
H. Choo, Highly efficient nanofocusing for integrated on-chip nanophotonics, Optoelectronics & Communications, Jan. 31, 2014, 3 pages, SPIE Newsroom DOI 10.1117/2.1201401.005275.
H. Choo, M. Kim, M. Staffaroni, T. J. Seok, J. Bokor, S. Cabrini, P. J. Schuck, M. Wu, E. Yablonovitch, Nanofocusing in a metal-insulator-metal gap plasmon waveguide with a three-dimensional linear taper, Nature Photonics, Nov. 18, 2012, p. 838-844, DOI: 10.1038/NPHOTON.2012.277.
L. A. Coldren, S. W. Corzine, Diode Lasers and Photonic Integrated Circuits, $2^{nd}$ Edition, Wiley Series in Microwave and Optical Engineering, 2012, 218.
J. Conway, Efficient Optical Coupling to the Nanoscale, Ph.D. thesis, Department of Electrical Engineering, University of California, Los Angeles, 2006, 165 pages.
T. W. Ebbesen, H. J. Lezec, H. F. Ghaemi, T. Thio, P. A. Wolff, Extraordinary optical transmission through sub-wavelength hole arrays, Nature, Feb. 12, 1998, p. 667-669, vol. 391.
D. K. Gramotnev, S. I. Bozhevolnyi, Plasmonics beyond the diffraction limit, Nature Photonics, Jan. 29, 2010, p. 83-91,vol. 4, DOI: 10.1038/NPHOTON.209.282.
D. S. Kim, S. C. Hohng, V. Malyarchuk, Y. C. Yoon, Y. H. Ahn, K. J. Yee, J. W. Park, Microscopic origin of surface-plasmon radiation in plasmonic band-gap nanostructures, Physical Review Letters, Oct. 3, 2003, p. 143901-2-5, vol. 91, No. 14.
S. Lloyd, Ultimate physical limits to computation, Nature, Aug. 31, 2000, p. 1047-1054, vol. 406.
S. A. Maier, Plasmonics: Fundamentals and Applications, Centre for Photonics and Photonic Materials, Department of Physics, University of Bath, UK, Springer, 2007, 234 pages, New York.
D. A. B. Miller, Device requirements for optical interconnects to silicon chips, Proceedings of the IEEE, Jul. 2009, p. 1166-1185, vol. 97, No. 7.
D. F. P. Pile, D. K. Gramotnev, Adiabatic and nonadiabatic nanofocusing of plasmons by tapered gap plasmon waveguides, Applied Physics Letters 89, Jul. 25, 2006, p. 041111, 4 pages.
B. Razavi, Design of Integrated Circuits for Optical Communications, McGraw-Hill, New York, Jul. 2002, 382 pages.
V. M. Shalaev, Transforming light, Science, Oct. 17, 2008, p. 384-386, vol. 322.

* cited by examiner

MEDICAL SENSOR HAVING A NANOSCALE TAPERED WAVEGUIDE FOR SPECTROSCOPY-BASED ANALYSIS OF FLUID

CROSS-REFERENCES TO RELATED APPLICATIONS

This application claims the benefit of U.S. Provisional Applications No. 62/175,078, filed Jun. 12, 2015 and 62/201,383, filed Aug. 5, 2015, the contents of which are hereby incorporated in their entireties for all purposes.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

A living being is subject to various health conditions. Medical diagnostic techniques have been developed to detect and monitor many of these conditions. For example, fluids of the living being contain molecules and other elements that are available for medical diagnostic. Particular analytes when identified in a fluid indicates a health condition.

Spectroscopy is a powerful diagnostic technique available to analyze fluids. Generally, spectroscopy involves emitting light towards a fluid and analyzing the spectrum of the light dispersed back. Dispersed light at a particular frequency acts as a fingerprint of a particular analyte, thereby diagnosing the respective health condition.

In a specific example, molecules in the fluid exhibit molecular rotations, molecular vibration, and electronic states in response to the emitted light. Molecular spectra can be observed from such energetic states and analyzed, using various spectroscopy techniques. For instance, microwave spectroscopy is available to analyze the molecular rotations. In comparison, infrared spectroscopy and Raman spectroscopy are available to analyze molecular vibrations. Further, ultraviolet spectroscopy and fluorescence spectroscopy are available to analyze electronic states.

Any of the above spectroscopy techniques can reliably diagnose the presence of an analyte. However, the sensitivity of these techniques depend on the concentration of the analyte in a volume of the fluid subject to excitation light. For instance, the larger the amount of the analyte, the more reliable the technique becomes. Conversely, the smaller the number, the less sensitive the spectroscopy technique can become.

BRIEF SUMMARY OF THE INVENTION

Generally described is a medical sensor. In an example, the medical sensor includes a substrate and a nanoscale tapered waveguide attached to the substrate. The nanoscale tapered waveguide includes a receiving channel having a height within a range of 250 nm to 750 nm and a width within a range of 150 nm to 250 nm. The receiving channel is formed by at least a first portion of a first rail and a first portion of a second rail. The first portions are substantially parallel to each other. The receiving channel is configured to receive fluid and guide an excitation light. The nanoscale tapered waveguide also includes a linearly tapered channel configured to receive the fluid and focus the excitation light guided from the receiving channel. The linearly tapered channel is formed by at least a second portion of the first rail and a second portion of the second rail. The second portions are linearly tapered relative to each other along two axes. The nanoscale tapered waveguide further includes an optical response channel configured to receive the fluid and to output a response light to the excitation light focused from the linearly tapered channels. The optical response channel is formed by at least a third portion of the first rail and a third portion of the second rail. The third portions are substantially parallel to each other. The optical response channel has a height within a range of 40 nm to 120 nm and a width within a range of 10 nm to 20 nm. The response light is based on a response of an analyte of the fluid to the excitation light focused from the linearly tapered channel.

Generally also described is a medical diagnostic method. In an example, the medical diagnostic method includes receiving fluid of a subject in a nanoscale channel of a nanoscale tapered waveguide. The medical diagnostic method also includes receiving an excitation light in a receiving channel of the nanoscale channel and guiding, by the receiving channel, the excitation light into a linearly tapered channel of the nanoscale channel. The linearly tapered channel is connected to the receiving channel. The medical diagnostic method further includes focusing, by the tapered channel, the excitation light guided from the receiving channel into an optical response channel of the nanoscale channel. The optical response channel is connected to the linearly tapered channel and includes an analyte of the fluid. The medical diagnostic method also includes outputting, from the optical response channel, a response light emitted from the analyte in response to the excitation light focused from the tapered channel. The response light is indicative of a medical condition of the subject.

Generally also described is medical diagnostic system. In an example, the medical diagnostic system includes a light source configured to emit an excitation light. The medical diagnostic system also includes a medical sensor. In turn, the medical sensor includes a nanoscale tapered waveguide comprising a nanoscale channel. The nanoscale channel is formed by at least a first rail and a second rail and is configured to receive fluid. A receiving channel of the nanoscale channel is further configured to guide the excitation light, a linearly tapered channel of the nanoscale channel is further configured to focus the excitation light guided from the receiving channel, and an optical response channel of the nanoscale channel is further configured to output a response light emitted from an analyte of the fluid in response to the excitation light focused from the linearly tapered channel. The medical diagnostic system further includes a light detector configured to detect the response light. The medical diagnostic system also includes a computing system communicatively coupled to the light detector. The computing system is configured to diagnose a medical condition based on the response light detected by the light detector.

DETAILED DESCRIPTION OF THE INVENTION

The embodiments of the present disclosure are directed, among other things, medical diagnostic of analytes in fluids. A medical sensor that includes a nanoscale tapered waveguide is described. The nanoscale tapered waveguide represents a three dimensional nanoplasmonic photon compressor (3D NPC). The use of such a sensor can improve the sensitivity of the medical diagnostic. In an example, the medical sensor is used in connection with spectroscopy. The sensitivity can be increased by multiple orders of magnitude depending on the spectroscopy type and the configuration of the medical sensor. For instance, the medical sensor is configured to return resonant light for coherent anti-Stokes Raman spectroscopy (CARS). The sensitivity of the CARS analysis can be increased by nine orders of magnitude such that a single resonant molecule can be detected. In comparison, existing CARS analysis necessitate about 5,000 molecules. The sensitivity improvement is enabled by the nanoscale tapered waveguide of the medical sensor.

In particular, the nanoscale tapered waveguide intensifies the spectroscopy signal by several magnitude orders. To do so, the nanoscale tapered waveguide includes a nanoscale channel for receiving a fluid, while also receiving and focusing a spectroscopy signal, such as an excitation light. In other words, the nanoscale channel represents a simultaneous fluidic and optical channel having a nanoscale size. The nanoscale channel includes a receiving channel that receives and guides the spectroscopy signal, a linearly tapered channel that has three dimensional (3D) linear tapering and that focuses the spectroscopy signal guided from the receiving channel down to nanoscale, and an optical response channel that outputs a spectroscopy response from a resonant molecule of the fluid present in the optical response channel in response to the spectroscopy signal focused from the linearly tapered channel. Generally, the 3D geometry of the nanoscale channel can achieve highly efficient compression of photons into a very small nanoscale volume (e.g., the optical response channel). This nanoscale volume serves as a well-controlled spectroscopy hotspot. In an example, about seventy percent can of the excitation light can be focused, while existing sensors focus at best five to ten percent. Accordingly, a relatively higher intensity spectroscopy signal is possible to apply in the optical response channel. By applying the relatively higher intensity signal to the resonant molecule, the intensity of the resonant response is likewise increased, thereby enabling the single molecule detection.

In an example, the medical sensor includes a number of nanoscale tapered waveguides attached to a substrate. Arrays of input and output grating couplers are also attached to the substrate. Each of the nanoscale tapered waveguides is disposed between the input and output arrays at particular input and output angles. An excitation light received by an input grating coupler is efficiently directed to a receiving channel of a nanoscale tapered waveguide given the input angle. Likewise, a response light outputted from the nanoscale tapered waveguide is efficiently directed outwards from an output grating coupler given the output angle.

In a further example, the medical sensor also includes a bag that encloses the different components of the medical sensor, such as the substrate, the nanoscale tapered waveguide(s), and the input and output arrays of grating couplers. The bag can be semi-permeable, thereby filtering elements from the fluids and preventing biofouling. For example, the bag is made of a thin layer of parylene-C. The filtering reduces undesired elements to reach the nanoscale tapered waveguide(s), thereby eliminating noisy signals that would have been otherwise generated by the undesired elements. The biofouling prevention extends the operational lifetime of the medical sensor when, for example, implanted in a subject such as a human being or an animal.

Generally, the medical sensor can be implanted in the subject in an area where fluid of the subject is present and can surround the medical sensor. Additionally or alternatively, the medical sensor can be inserted in a tube, or some other laboratory equipment, that contains the fluid. Regardless, a light source is used to emit a number of excitation lights towards the medical sensor. An excitation light has a wavelength that falls within a particular spectrum. For example, the excitation light is an infrared light, visible light to an unaided human eye, or ultraviolet light. Response light (e.g., resonant light) outputted from the medical sensor is detected by a light detector. A computing system analyzes the response light to detect a number of health conditions.

Accordingly, various health conditions can be diagnosed and monitored over time. Depending on the fluid and/or location of the medical sensor within the subject, ophthalmology, neurology, endocrinology, gastroenterology, internal medicine, microbiology, allergy, immunology, and urology related diagnosis and monitoring are possible. Detectable analytes include human and non-human molecules such as electrolytes, blood components, plasma components, cells, protein, glucose, fat, enzymes, immunologic markers, acids, bases (and accordingly, pH of a fluid). In addition, molecules foreign to the subject can be detected. These molecules include, for example, viruses, bacteria, medications, drugs, and hazard substances.

In the interest of clarity of explanation, the embodiments of the present invention are described in connection with CARS, molecules, and the monitoring of dehydration. However, the embodiments are not limited as such. Instead, the medical sensor can be used in connection with other spectroscopy (e.g., RAMA and fluorescent) and medical diagnostic techniques, to detect other analytes, and/or to identify other medical conditions.

Figure 1:
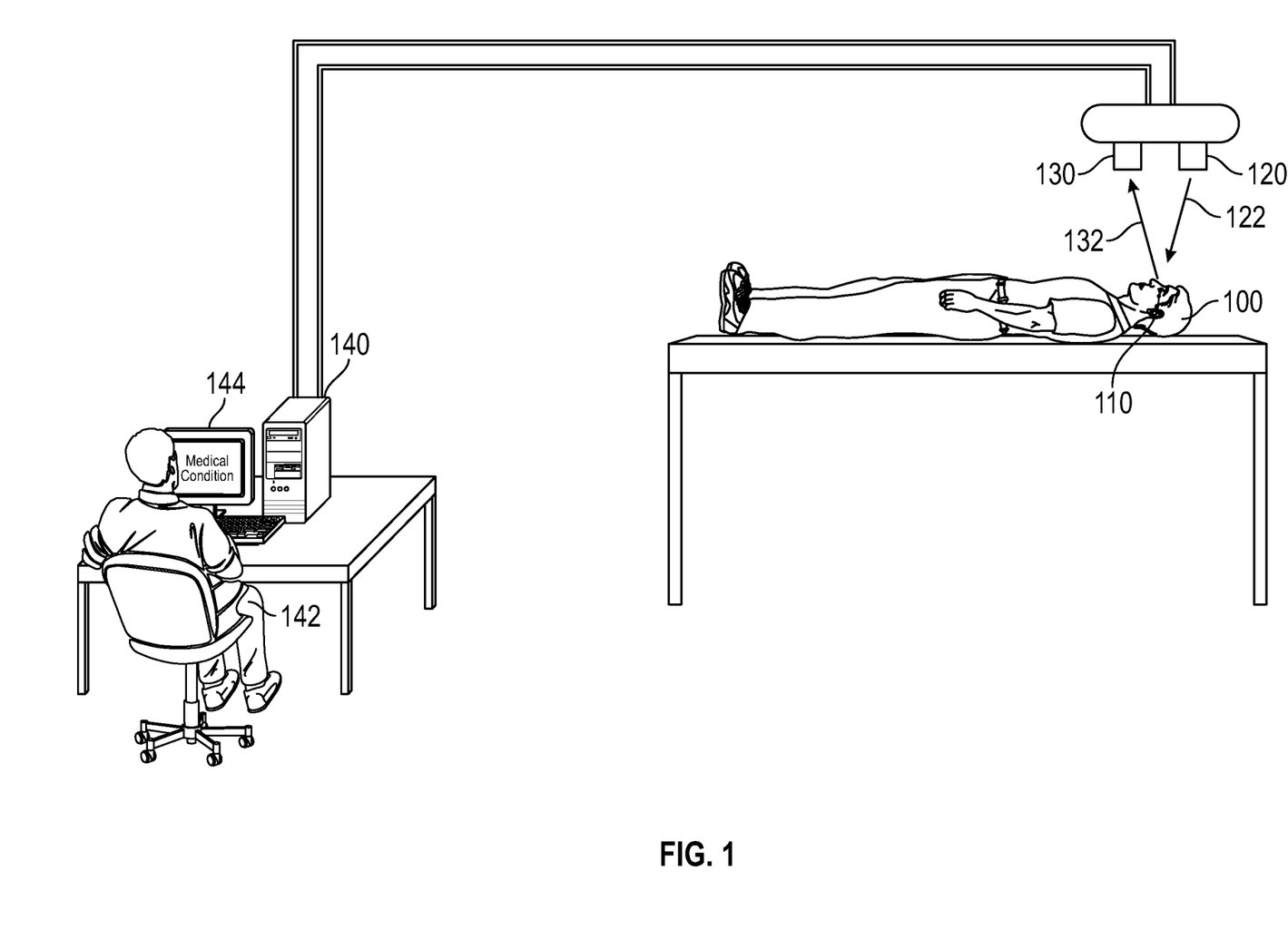
FIG. 1 illustrates an example operational environment for diagnosing a health condition of a subject.

FIG. 1 illustrates an example operational environment for diagnosing a health condition of a subject 100. As illustrated, the operational environment includes a medical sensor 110, a light source 120, a light detector 130, and a computing system 140. An operator 142, such as a medical professional, operates the computing system 140 to diagnose the health condition.

The different components are illustrated as being separate. Nonetheless, the embodiments of the present disclosure are not limited as such. Instead, some or all of the illustrated components can be integrated. For example, the light source 120, the light detector 130, and the computing system 140 can be integrated into a single handheld device. Further, although the medical sensor 110 is illustrated as being implanted in the subject 100, no implantation may be needed. Instead, fluid of the subject 100 and the medical sensor 110 can be added to a same laboratory equipment, such as a tube, for analysis.

In an example, the medical sensor 110 includes a number of components, such as a substrate, a set of nanoscale tapered waveguides, a set of input grating couplers, a set of output grating couplers, and a semi-permeable membrane forming a bag around these component. The components are further described in the next figures.

Fluid of the subject 100 enters the nanoscale tapered waveguide(s). In addition to receiving the fluid, the medical sensor 110 acts a passive sensor that receives one or more excitation lights 122 from the light source 120 and, in response, outputs response lights 132 to the light detector 130. An excitation light 122 has a particular frequency or wavelength and can cause a change to a property of a molecule (e.g., molecular rotation, molecular vibration, electronic state), where the molecule is present in an optical response channel of a nanoscale tapered waveguide of the medical sensor 110. This change in property is exhibited as a response light. The response light 132 can have a different frequency or wavelength that helps identify the molecule.

In the example use case of CARS, the diagnosis involves three laser beams: a pump beam of frequency, a Stokes beam of frequency, and a probe beam at frequency. The pump beam and Stokes beam are focused into the optical response channel to interact with molecules thereat and generate a coherent optical signal at the anti-Stokes frequency. The latter is resonantly enhanced when the frequency difference between the pump and the Stokes beams coincides with the frequency of a Raman resonance (e.g., vibration resonance of a molecule).

In an example, the light source 120 is configured to emit excitation lights 122 that meet various medical standards, such as ones defined by the American National Standards Institute (ANSI). Accordingly, the excitation lights 122 are not harmful to the subject 100. In the example use case of CARS, low power excitation lights 122 in the near infrared range of 750 nm to 1150 nm are used. Other excitation lights 122 may be possible in the infrared spectrum, ultraviolet spectrum, and/or visible spectrum.

In an example, the light detector 130 is configured to detect the response 132 light. Signal processors of the light detector 130 generates data from the response light 132, where the data is indicative of an observed light spectrum. The data is transmitted to the computing system 140 over a data network and/or a communication bus.

In an example, the computing system 140 represents a head end computer that analyzes the response spectrum (e.g., the observed data indicative thereof) and/or controls medical-related operations. Observed data can be received from the light detector 130 over a data network or a communication bus. Conversely, control instructions can be sent to the light detector 130 and light source 120 over the same or different data network or communication bus. The control instructions enable, for instance, the operator 142 to control parameters related to the positioning of the light source 120 and light detector 130 relative to the subject 100, parameters related to the excitation lights 122 (e.g., direction, intensity, duration, wavelength, and other light-related parameters), and parameters related to response light 122 (e.g., filtering of undesired spectrum, sampling rate).

Generally, the computing system 140 includes a memory, a processor, and user input/output devices (e.g., a display, keyboard, mouse, etc.). The observed data is provided to the memory. The control instructions are provided from the memory. Any suitable memory can be used such as RAM and/or ROM memories. The memory hosts a medical application that is executed by the processor. Any suitable processor can be used such as a general central processing unit (CPU). A user interface (UI) is available on one of the input/output devices (e.g., the display) to interface with the medical application. Any suitable display, of any suitable size and/or type, can be used to provide the UI. The UI enables the operator 142 to interface with the medical application.

The medical application provides various medical-related functionalities. For example, the medical application facilitates medical diagnosis based on the observed data indicative of the response light 132 detected by the light detector 130, and controls over the light source 120 and light detector 130. The medical diagnosis involves a spectroscopy analysis of the response light 132 to identify peaks (e.g., resonant frequencies) and or responses at particular frequencies (or, conversely, wavelengths). The peaks, or more generally, the responses, identify particular molecules. The presence of the molecules indicate one or more health conditions. The medical application has access from the local memory or from remote storage to correlations between the responses and health conditions. Accordingly, the medical application identifies the one or more health conditions from the correlations and presents (e.g., visualizes) the identified health conditions 144 on an interface (e.g., the UI) of the computer system 140. The medical analysis also enables the operator 142 to visualize the observed spectrum and the associated raw data.

Hence, by operating the light source 120, light detector 130, and computing system 140, the operator 142 can diagnose a health condition of the subject 100 based on the response light 132 emitted from the medical sensor 110. Because the medical sensor 110 includes a number of nanoscale tapered waveguides, the sensitivity of the observations can be down to a single molecule in the example use case of CARS.

Figure 2:
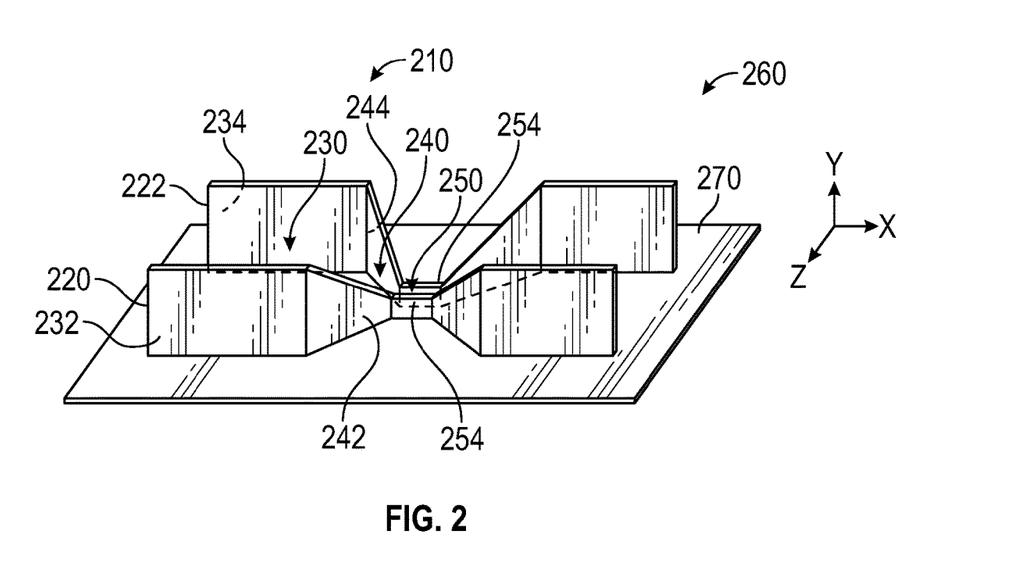
FIG. 2 illustrates an example nanoscale tapered waveguide, which can be a component of the medical sensor.

FIG. 2 illustrates an example nanoscale tapered waveguide 200, which can be a component of the medical sensor 110. In an example, the nanoscale tapered waveguide 200 is configured as a bidirectional waveguide. In other words, an excitation light can be received at either ends of the nanoscale tapered waveguide 200 and a response light can be outputted on the opposite, non-receiving end. FIG. 2 illustrates this bidirectionality by showing the nanoscale tapered waveguide 200 as including a left hand portion 210 and a right hand portion 260 that mirror each other and that are connected at a center location relative to the two portions 210 and 260.

In the interest of explanation, components of the left hand portion 210 are further described herein. The right hand portion 260 has equivalent components. Further, although the nanoscale tapered waveguide 200 is bidirectional, a nanoscale tapered waveguide need not be bidirectional. Instead, the embodiments of the present disclosure include unidirectional nanoscale tapered waveguides (e.g., a waveguide formed by the left hand portion 210 without the right hand portion 260).

As illustrated, two rails 220 and 222 form the nanoscale tapered waveguide 200. The thickness of each rail 220 and 222 fall in the range of 25 nm to 600 nm. In an example, this thickness is about 300 nm across the different channels. The rails 220 and 222 can but need not be made of the same material. In an example, a biocompatible material, such as gold, can be used for the rails 220 and 222.

Focusing on the left hand side portion 210, the rails 220 and 222 form a nanoscale channel. Generally, the nanoscale channel represents a nanoscale gap between the rails 220 and 222, where the nanoscale gap is configured for receiving fluid, receiving an excitation light, focusing the light, and outputting a response light from the fluid in response to the focused excitation light. In an example, the nanoscale channel includes a receiving channel 230, a linearly tapered channel 240, and an optical response channel 250.

In an example, a first portion 232 of the first rail 220 and a first portion 234 of the second rail 222 are substantially parallel to each other and separated by a certain distance, thereby forming the receiving channel 230. The receiving channel 230 can have a uniform geometric shape, such as a rectangular shape, across the first portions 232 and 234. As defined by the first portions 232 and 234, the length (e.g., distance along the X axis from a first end of the receiving channel 230 and an opposite, connected end of the linearly tapered channel 240), height (distance along the Y axis), and width (e.g., distance along the Z axis between the two rails), of the receiving channel 230 fall within a length range, a height range, and a width range, respectively. The length range is 1 µm to 2 µm. The height range is 250 nm to 750 nm. The width range is 150 nm to 250 nm. In an illustrative example, the length, width, and height of the receiving channel 230 are about 1.5 µm, 600 nm, and 200 nm, respectively.

In an example, a second portion 242 of the first rail 220 and a second portion 244 of the second rail 222 are substantially tapered relative to each other, thereby forming the linearly tapered channel 240. A connection end connects the second portion 242 to the first portion 232 of the first rail 220. Likewise, a connection end connects the second portion 244 to the first portion 234 of the second rail 222. Accordingly, the linearly tapered channel 240 is connected to the receiving channel 230 at the connection ends. The tapering is inward (e.g., at a right angle) relative to the connection ends such that ends opposite to the connection ends would intersect. The tapering can be three dimensional (3D) and linear to define a pyramid-like geometric shape of the linearly tapered channel 240. A base of the pyramid is at the connection ends. For instance, the tapering occurs laterally and vertically (e.g., along the Z and Y axes) at respective tapering angles. The tapering angles can but need not be the same and are generally right angles. For example, a tapering angle along a lateral direction falls in the range of fifteen to forty degrees. Similarly, a tapering angle along the vertical direction falls in the rage of fifteen to thirty-five degrees. In an illustrative example, the tapering angles are set at about twenty-nine degrees. Based on the tapering angles, a certain dimension of the linearly tapered channel 240 is defined. For example, width and height of the linearly tapered channel 240 at the connection ends (e.g., at the base of the pyramid) fall within the range of 150 nm to 250 nm and 250 nm to 750 nm, respectively. In an illustrative example, the width and height are about 200 and 600 nm, respectively. At opposite ends, the width and height fall within the range of 10 nm to 20 nm and 40 nm to 120 nm, respectively. In an illustrative example, the width and height are about 14 nm and 80 nm, respectively.

In an example, a third portion 252 of the first rail 220 and a second portion 254 of the second rail 222 are substantially parallel to each other and separated by a certain distance, thereby forming the optical response channel 250. A connection end connects the third portion 252 to the second portion 242 of the first rail 220. Likewise, a connection end connects the third portion 254 to the second portion 244 of the second rail 222. Accordingly, the optical response channel 250 is connected to the linearly tapered channel 240 at the connection ends (e.g., at the tip of the linearly tapered channel 240). The optical response channel 250 can have a uniform geometric shape, such as a rectangular shape, across the third portions 252 and 254. As defined by the third portions 252 and 254, the width and height of the optical response channel 250 fall within the range of 10 nm to 20 nm and 40 nm to 120 nm, respectively. In an illustrative example, the width and height are about 14 and 80 nm, respectively. The length of the optical response channel 250 (e.g., distance along the X axis between the connection ends and starting ends of an equivalent optical response channel of the right hand portion 260) falls within the range of 150 nm to 250 nm. In an illustrative example, the length is about 200 nm.

In an example, the rails 220 and 222 are connected to a substrate 270 at a connection angle. The substrate 270 can be made of a biocompatible material, such as silicone dioxide ($SiO_2$), or some other biocompatible dielectric. In an illustrative example, each of the two rails 220 and 222 is connected to the substrate 270 along at about ninety degrees. FIG. 2 shows this connection along the XZ plane.

Figure 3:
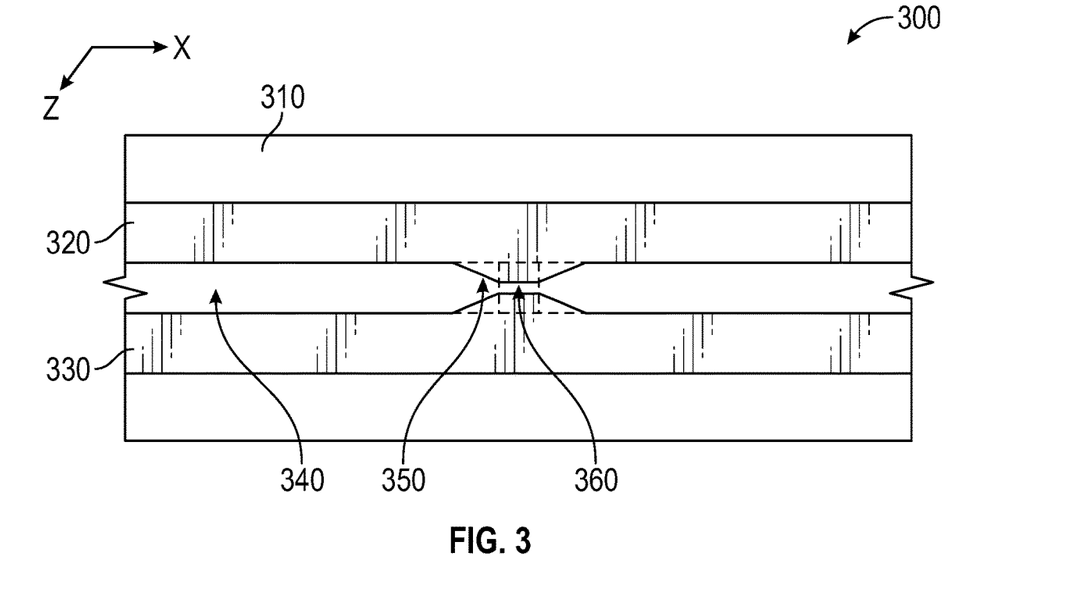
FIG. 3 illustrates a cross-section view of a nanoscale tapered waveguide.

FIG. 3 illustrates a cross-section view of a nanoscale tapered waveguide 300, such as a view of the waveguide 200 along the XZ plane of FIG. 2. As illustrated, $SiO_2$ forms a substrate 310. Two gold rails 320 and 330 sit on top of the substrate 310, forming walls at about ninety degrees relative to the substrate 310. The two gold rails 320 and 330 form left hand side and right hand side portions of the nanoscale tapered waveguide 300. In each of the sides, the walls and the substrate 310 define a receiving channel 340, linearly tapered channel 350, and an optical resonance channel 360.

In an example, the thickness of each gold rail 320 and 330 along the Z axis is about 300 nm. The distance between the inner surfaces of the walls along the Z axis is about 200 nm in the receiving channel 340, 200 nm at the base of the linearly tapered channel 350, 14 nm at the tip of the linearly tapered channel 350, and 14 nm in the optical response channel 360. The tapering angle, relative to the X axis is about twenty-nine degrees.

The tapering angle and the distance at the tip of the linearly tapered channel 350 can be selectively designed according to a number of parameters. The parameters include molecule-related parameters and light-related parameters. For example, the distance may be designed to be large enough to accept particular molecules or particular molecular compositions. In another example, the larger the distance is, the smaller the light intensity enhancement is. This relationship can be non-linear.

Figure 4:
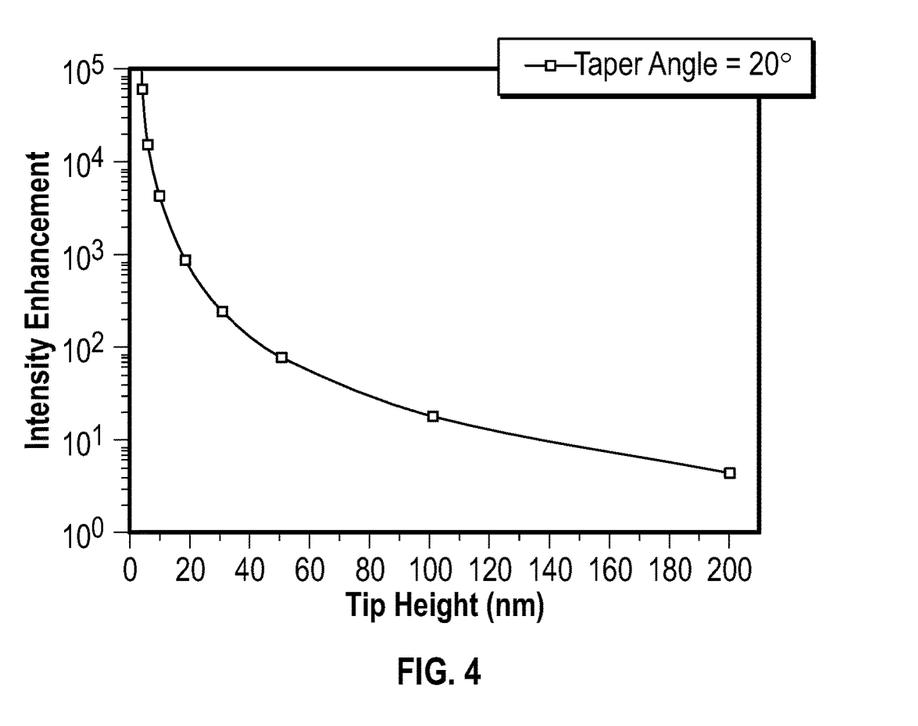
FIG. 4 illustrates an example non-linear relationship between the distance at a tip of nanoscale tapered waveguide and light intensity enhancement.

FIG. 4 illustrates an example non-linear relationship between the distance at the tip and the light intensity enhancement at a twenty degree tapering angle. As illustrated, at about a 14 nm distance and 20 degree tapering angle, the light intensity enhancement is about $10^4$.

Figure 5:
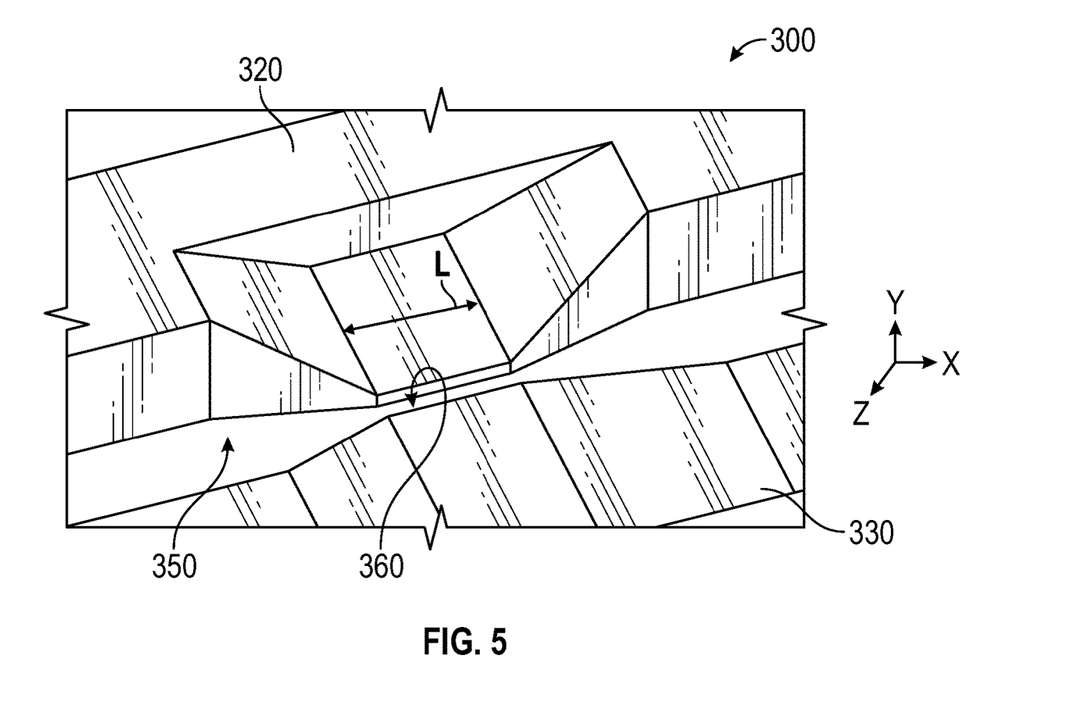
FIG. 5 illustrates a perspective view of a nanoscale tapered waveguide.

FIG. 5 illustrates a perspective view of the nanoscale tapered waveguide 300 of FIG. 3. The perspective view focuses on the linearly tapered channel 350 and the optical response channel 360. As illustrated, the walls that form the linearly tapered channel 350 also define 3D linear tapering. The 3D linear tapering occurs laterally and vertically (e.g., along the Z and Y axes, respectively). This tapering defines a linear transition from a distance along the Z axis (e.g., width) of about 200 nm at the base of the linearly tapered channel 350 to about 14 nm at the tip of the linearly tapered channel 350. The tapering defines a linear transition from a distance along the Y axis (e.g., height) of about 600 nm at the base of the linearly tapered channel 350 to about 80 nm at the tip of the linearly tapered channel 350.

Within the optical response channel 360, the walls maintain the width and height at about 14 nm and 80 nm, respectively, and define a distance along the X axis (e.g., length) of about 200 nm.

In an example, a manufacturing process of the nanoscale tapered waveguide 300 removes portions of the gold rails 320 and 330 to form a notched area around the 3D linear tapering. Nonetheless, the embodiments of the present disclosure are not limited as such. For example, the notched area is not created. Instead, the gold corresponding to the notched area is not removed during the manufacturing process.

Various manufacturing processes are available to manufacture the medical sensors shown in the figures of the present disclosure. Example of such manufacturing processes include nanofabrication, lithography, and nanoimprint. In an example, nanoscale milling, deposition, and/or lithography is applied to a $SiO_2$ substrate to create a nanoscale channel of a desired geometry. Subsequently, gold is deposited in the nanoscale channel. Milling and/or etching is applied to the gold to create rails that define a receiving channel, a linearly tapered channel, and an optical response channel.

Figure 6:
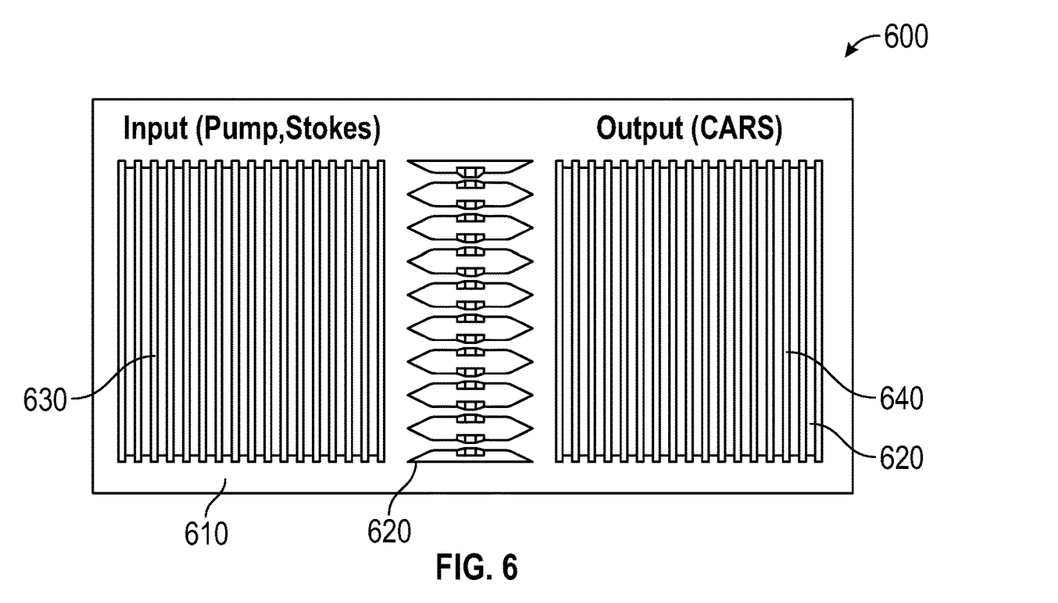
FIG. 6 illustrates example input and output arrays of grating couplers and example array of nanoscale tapered waveguides.

FIG. 6 illustrates example input and output arrays of grating couplers and example array of nanoscale tapered waveguides. These different arrays can form components of a medical sensor 600, such as the medical sensor 110 of FIG. 1.

As illustrated, the medical sensor 600 includes a substrate 610. An array 620 of nanoscale tapered waveguides sits on top of the substrate 610. Each of the nanoscale tapered waveguides can include some or all of the components of the nanoscale tapered waveguide 200 of FIG. 2. The waveguide array 620 is positioned between an input array 630 of grating couplers and an output array 640 of grating couplers. In turn, the input array 630 and output array 640 sit on top of the substrate 610.

The input array 630, the waveguide array 620, and the output array 640 can be positioned relative to each other according to a geometric configuration that optimizes the efficiency of propagating light through the medical sensor 600. For example, each of the input array 630 and output array 640 includes a set of blazed grating couplers having particular blaze angles (e.g., grating couplers according to a particular Littrow configuration), such as in the range of forty-five to sixty degrees. The input array 630 directs an excitation light from a first direction to second direction at about, for example, a ninety degree angle. Conversely, the output array 640 redirects a response light from the second direction back to the first direction at about, for example, the ninety degree angle. The nanoscale tapered waveguides are oriented parallel to each other along the second direction. In an example, the waveguide array 620 sits at about ninety degrees relative to each of the input array 630 and output array 640. In another words, a nanoscale tapered waveguide of the waveguide array 620 can receive an excitation light and outputs a response light at the second direction, where the excitation light is emitted from a light source towards the input array 630 along the first direction, and where the output array 640 emits the response light towards a light detector back in the first direction.

Generally, the positioning of the input array 630, the waveguide array 620, and the output array 640 results in a stronger (e.g., more intense) response light relative to other possible positioning. However, the illustrated positioning may result in a directional medical sensor. In other word, the strong response light may be outputted in the second direction if an excitation light is received in the first direction.

In an example, each of the input array 630, the waveguide array 620, and the output array 640 includes about one hundred input grating couplers, one hundred nanoscale tapered waveguide, and one hundred output grating couplers. The dimensions of this arrangement are about 100 μm by 1,000 μm in width and length.

Figure 7:
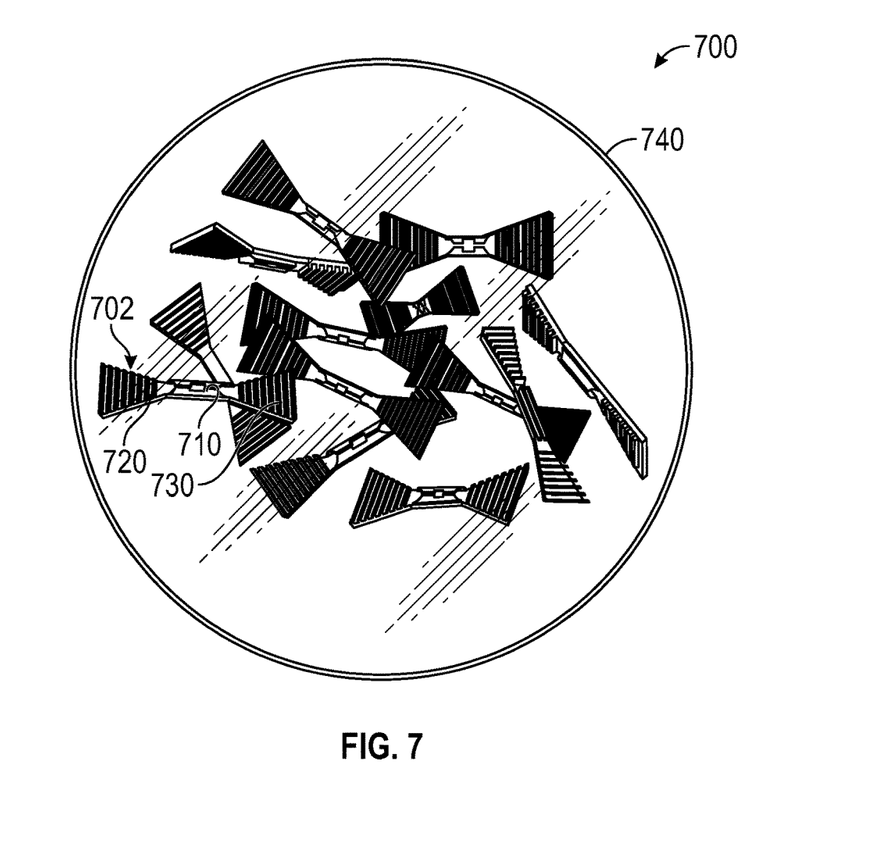
FIG. 7 illustrates another example configuration of input and output arrays of grating couplers.

FIG. 7 illustrates another example configuration of input and output arrays of grating couplers. These different arrays can form components of a medical sensor 700, such as the medical sensor 110 of FIG. 1.

As illustrated, the medical sensor 700 includes a plurality of sensing portions 702 and a bag 740. In turn, each sensing portion 702 includes at least one nanoscale tapered waveguide 710, an input array 720 of grating couplers, an output array 730 of grating couplers. The bag 740 contains the plurality of sensing portions 702. The plurality of sensing portions are randomly oriented inside the bag 740.

Generally, the random orientation may result in a multi-directional medical sensor. In other words, a response light may be outputted in a direction in response to an excitation light received in almost any direction. However, the response light may not be as strong as the one of the directional medical sensor of FIG. 6.

In an example the bag 740 is made of a semi-permeable polymer, such as parylene-C or silicone. The thickness of the polymer can vary in the range of 0.5 μm to 1.5 μm. Generally, the semi-permeability of the bag 740 enables filtering of components present in the examined fluid and preventing of biofouling. The diameter of the bag 740 depends on the number of sensing portions 702. In an illustration, about 10,000 sensing portions are included. In this illustration, the diameter of the bag 740 is less than two millimeters.

Figure 8:
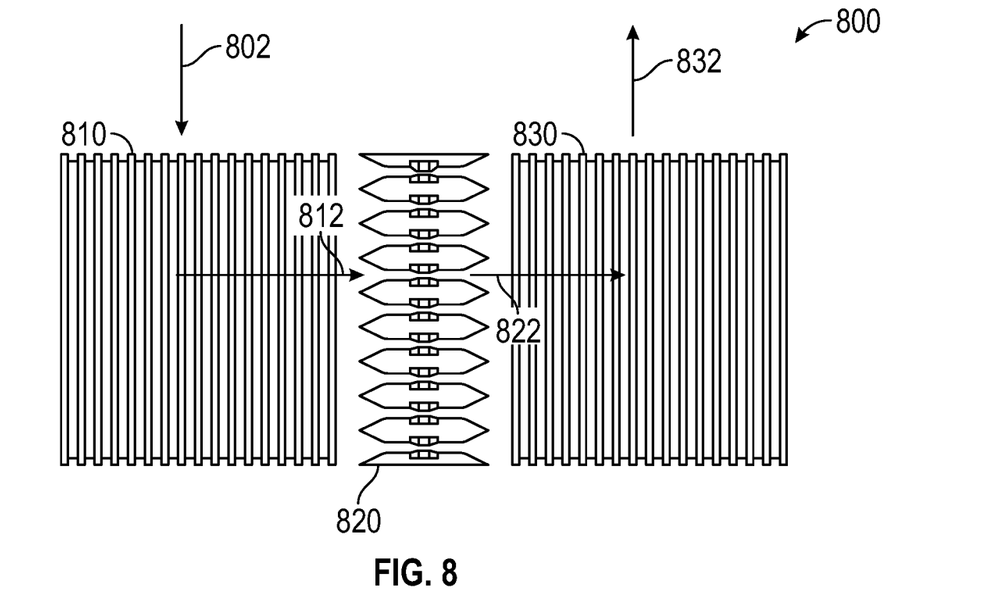
FIG. 8 illustrates an example propagation of an excitation light through a medical sensor.

FIG. 8 illustrates an example propagation of an excitation light 802 through a medical sensor 800. The medical sensor 800 outputs a response light 832 in response to the excitation light. FIG. 8 illustrates the use of an input array 810 of grating couplers, an array 820 of nanoscale tapered waveguide, and an output array 830 of grating couplers having a similar arrangement as the one illustrated in FIG. 6. The arrangement illustrated in FIG. 7 also results in a similar propagation and output based on the respective components.

As illustrated, the input array 810 receives the excitation light 802 from an external source. In the interest of clarity of explanation, FIG. 8 illustrates the excitation light 802 as a single light beam. Nonetheless, the excitation light 802 may be wider and can be received by a large number or all of the grating couplers of the input array 810. According to the blaze angle, the input array 810 redirects the excitation light 802 into the waveguide array 820. FIG. 8 illustrates the redirected excitation light as excitation light 812.

Next, the waveguide array 820 receives the excitation light 812 from the input array 810 and outputs a response light 822. For example, some or all of the nanoscale tapered waveguides receive the excitation light 812. Each receiving nanoscale tapered waveguide focuses the excitation light onto molecules of fluid present in the nanoscale tapered waveguide. A response light is emitted based on responses (e.g., changes to properties) of some of the molecules. Collectively, response lights from the different molecules and the nanoscale tapered waveguides are illustrated as the response light 822 in FIG. 8. The waveguide array 820 emits the response light 822 towards the output array 830.

The output array 830 receives the response light 822 from the waveguide array 820. According to the blaze angle, the output array 830 redirects the response light 822 outwards from the medical sensor 800. FIG. 8 illustrates the redirected response light as response light 832. A light detector positioned along this outward direction can detect the response light 832.

Although FIG. 8 illustrates about ninety-degree angles for redirecting the excitation light and the response light, other redirection angles can be used. In addition, the two redirection angles need not be the same. Generally, a desired redirection angle is achieved based on, for example, the blaze angle of a grating coupler and the relative position and orientation of the grating coupler and a nanoscale tapered waveguide.

Figure 9:
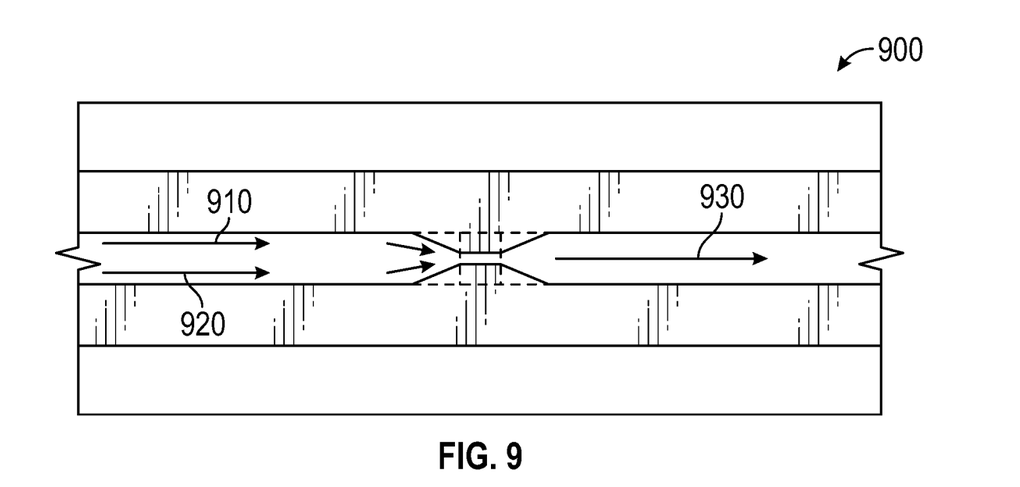
FIG. 9 illustrates an example propagation of an excitation light through a nanoscale tapered waveguide for coherent anti-Stokes Raman spectroscopy (CARS).

FIG. 9 illustrates an example propagation of an excitation light through a nanoscale tapered waveguide 900 for CARS. The nanoscale tapered waveguide 900 outputs a response light in response to the excitation light. The nanoscale tapered waveguide 900 can be a sensing portion of the waveguide array 820 of FIG. 8. The excitation light can correspond to the excitation light 812 of FIG. 8. The response light can correspond to the response light 822 of FIG. 8. Although CARS is illustrated, the nanoscale tapered waveguide 900 can be used for other types of spectroscopy by, for instance, varying the excitation light.

CARS is a third order nonlinear optical process in which a pump field $E_p$ at frequency $\omega_p$ and a Stokes field $E_s$ at frequency $\omega_s$ interact with a sample (e.g., fluid) to generate a signal field $E_{as}$ at the anti-Stokes frequency of $\omega_{as}=2\omega_p-\omega_s$. When $\omega_p-\omega_s$ is tuned to be resonant with molecular vibration ($\Omega$), the CARS signal can be significantly enhanced, producing a large vibrational contrast.

As illustrated in FIG. 9, the excitation light includes a pump beam 910 at frequency $\omega_p$ and a stokes beam 920 at frequency $\omega_s$. The nanoscale tapered waveguide 900 focuses the pump beam 910 and the stokes beam 920 into an optical response channel. Analytes (e.g., molecules) of a fluid present in the optical response channel exhibit vibration (e.g., molecular vibration). The vibration results in the response light 930, representing a CARS signal.

Generally, CARS is a powerful technique for detecting small and large analytes (e.g., molecules) of biological interests because the Raman spectrum provides unique molecular fingerprints of analytes. Blue-shifted from the excitation frequency, CARS signals can be easily detected even in the presence of the one-photon fluorescence background. Using excitation source in the near infrared range (750 nm to 1,150 nm) where biological tissues exhibit minimum absorption of light, CARS utilizes the molecular vibrations and avoid the use of any imaging markers and/or immunolabels. The strength of CARS signals depends only on the excitation intensity and the concentration of the vibrating molecules ($I_{CARS} \propto N_m^2 I_p^2 I_s$, where $I_p$ and $I_s$ are the intensities of the pump and Stokes beams, respectively). The process does not involve any surface chemistry or interactions necessary for many other nanoparticle-based sensor approaches such as surface enhanced Raman scattering (SERS). Since molecules need not possess electrochemical affinity to the sensor materials, the types of molecules that can be identified using CARS are almost unlimited, and CARS does not involved molecule-to-surface adsorption/reaction time, so fast and real time measurements can be made. Because CARS utilizes coherent Raman process, CARS signals are approximately $10^5$ times stronger than those generated by traditional Raman spectroscopy (RS) under the same measurement conditions. However, CARS, absent of the embodiments of the present disclosure, necessitates a significant amount (about 5,000) analytes in its beam focus for detection.

On the other hand, using CARS in combination with the embodiments of the present disclosure, can provide an additional enhancement factor over CARS by up to nine orders of magnitude. Therefore, the $10^5$ enhancement factor ($EF_{over\_Raman}$) observed by CARS over RS can be increased to $10^{14}$. The theoretical upper limit of combined CARS intensity enhancement by a single nanoscale tapered waveguide is predicted to be $10^{15}$ at a loss of 3 dB, which easily outweighs the loss in CARS intensity due to the decreased number of analytes in the smaller volume of the spectroscopy hotspot (e.g., the optical response channel). At this level of CARS emission enhancement, a single nanoscale tapered waveguide can detect a single molecule of glucose vibrating its hotspot. Given the same excitation conditions, simulated results indicate that CARS emission from each individual hotspot (200-by-50-by-10-nm³ or $10^5$ nm³ by volume) in a nanoscale tapered waveguide is about $10^5$ times stronger than that from a focal spot formed by a NA=1.4 objective lens. By creating the arrays of nanoscale tapered waveguides and grating couplers, additional CARS enhancement of $10^4$ can be obtained. Hence, the total enhancement factor (TEF) of the medical sensors described herein over the traditional Raman measurement can be expressed as TEF =

$$(EF_{overRaman}) \times \left[\frac{(\text{Intensity Enhancement}_{by\,NPC})^3}{(\text{No. of molecules lost})^2 = (Vol_{len\,focus}/Vol_{hotspot})^2}\right] \times$$

$$(\text{No. of } NPCs) = (10^5) \times \left[\frac{(10^4)^3}{(0.25\,\mu m^3/10^5 nm^3)^2}\right] \times (10^4) \sim 10^{14}.$$

This $10^{14}$ total enhancement factor makes it possible for single molecule detection. For an example, to detect 0.2 mM of glucose in tear within a 200-by-50-by-10-nm³ volume, only an enhancement of $10^{12}$ is needed, where approximately 10 molecules are in the hotspot volume. If there is only 1 molecule, an additional $10^2$ enhancement is needed. Because the total enhancement is larger than $10^{14}$, it is possible for single-molecule detection using medical sensors described herein.

In addition, the use of such medical sensors makes it possible to sample analytes over a larger area, generating more reliable average values. Because nanoscale tapered waveguides focus on hotspots with extremely high intensity, the excitation beam that is externally applied can be significantly below the laser power level allowed in medical application. Moreover, the volume of the CARS hotspot (e.g., the optical response channel) in a nanoscale tapered waveguide is well defined, which allows precise calculation of molecular concentration within the volume, and any background emission can be well suppressed. Accordingly, such medical sensors can allow single-molecule sensitivity and specificity on virtually any molecule with a unique CARS signature, thereby enabling researchers to achieve in vivo, ex vivo, and in vitro biochemical analysis with unprecedented accuracy and precision.

Examples of biochemical analysis include measuring human/animal analyte from any biological fluid or any fluid. Example detectable molecules include electrolytes, blood components, plasma components, cells, protein, glucose, fat, enzymes, immunologic markers, acids, bases. Additionally, the pH of a fluid can be measured. The biochemical analysis can also measure the presence of nonhuman molecules inside a body like virus, bacteria, medication, drugs, or hazard substance.

As described herein above, a nanoscale tapered waveguide increases the intensity of excitation light by several orders of magnitude. The nanoscale tapered waveguide condenses the excitation laser power into a nanoscale volume very efficiently through a 3D linearly tapered channel and dramatically increase the laser's intensity. Further, the nanoscale tapered waveguide includes nanofluidic channels that also serve as waveguides (or guided light passages) for excitation light as well as resulting CARS emission. In the center of nanoscale tapered waveguide, a well-defined hotspot (e.g., an optical response channel) is defined, where the dimensions of this hotspot are about 200-by-50-by-10 nm$^3$ volume, with an intensity enhancement of about $10^4$. This intensity enhancement can be expressed as I $$E = \frac{|E|^2}{|E_0|^2} = \frac{A_{inc.}}{A_{channel}} \times \eta^2,$$

where $A_{inc.}$ and $A_{channel}$ are modal areas of incidence Gaussian beam and the tip of the hotspot, respectively. In this calculation, the diameter of the incidence Gaussian beam and the coupling efficiency ($\eta$) are assumed as 500 nm and 50%, respectively. In addition, grating structures (e.g., the input and output grating couplers of FIGS. 7 and 8) are designed for the efficient coupling of the y-polarized input beam to the structure as well as coupling out the CARS emission from the device for remote detection. This substantial $10^4$ enhancement in excitation intensity translates to CARS-signal enhancement on the order of $10^{12}$, which is sufficient for ten glucose molecules in the hotspot. Considering the decrease in the volume (and consequently decrease in the number of vibrating molecules in the hotspot by a factor of about $10^3$), the final CARS enhancement will be greater than $10^5$ for a single nanoscale tapered waveguide when compared to CARS emission from a focal point formed by a 1.4 NA objective lens. When an array of such nanoscale tapered waveguides is arranged in a medical sensor as illustrated in FIG. 6, the total enhancement factor over the traditional Raman measurement is about $(10^5)(10^5)(10^4)=10^{14}$, which makes it possible to detect a single molecule. Another way to utilize our 3D NPC is to freely release individual 3D NPCs from the substrate. When about 1,000 to 10,000 randomly oriented nanoscale tapered waveguides are enclosed in an implantable bag made of semipermeable membrane such as in the example arrangement of FIG. 7, it is possible to excite and detect at any directions. In this case, CARS enhancement will be on the order of about $5 \times 10^{13}$, which can still achieve single-molecule For quantitative measurements, a differential measurement technique can be used. In particular, two sensor units are implanted in a fluidic area of a subject. Each of the units can include a configuration of nanoscale tapered waveguides and grating couplers as described herein above. One unit outputs a light response from the fluid. The other unit is sealed (e.g., with a transparent permeable membrane) and includes a reference fluid. This unit outputs a light reference response. By comparing with the two responses, as with other reference values previously recorded, the precise number of analyte molecules in a unit volume can be calculated.

In addition, parylene-C is a readily proven biocompatible polymer with the highest USP class-VI classification and it has found numerous coating applications for medical devices such as pacemakers and drug-eluting stents. Ultrathin parylene-C could be used as semi-permeable material when the thickness is reduced to submicron range. For example, a 0.8 μm thick parylene-C has a molecular exclusion of 71 kD. With the control of the thickness, parylene-C membrane can have different tunable exclusion molecular weights, and can be used for the coating or sealing of the medical sensors described herein.

Figure 10:
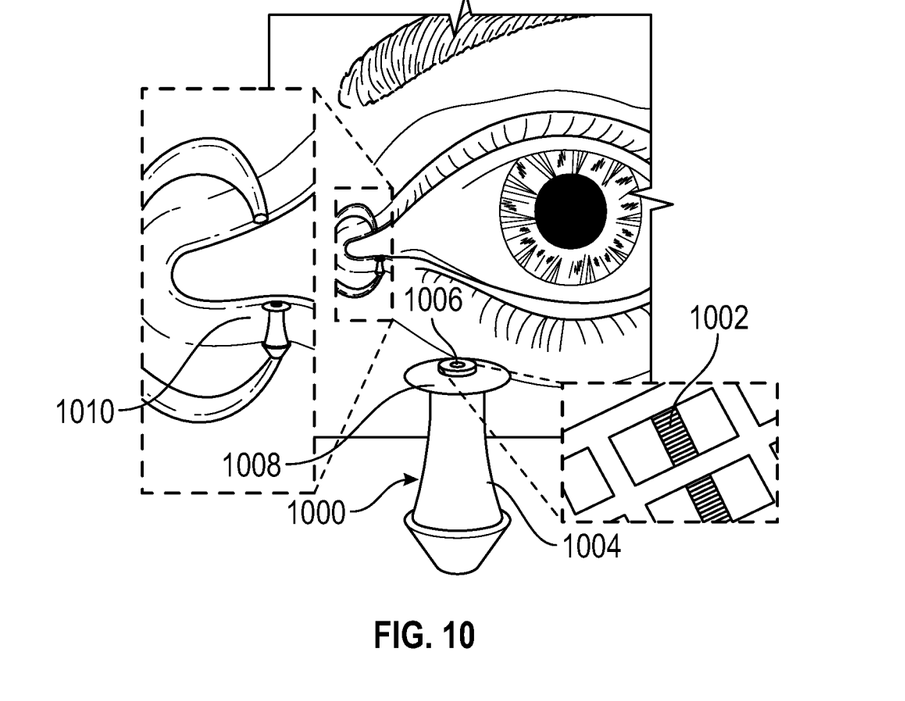
FIG. 10 illustrates an example use case of a medical sensor that includes arrays of nanoscale tapered waveguides.

FIG. 10 illustrates an example use case of a medical sensor 1000 that includes arrays 1002 of nanoscale tapered waveguides. The medical sensor 1000 is implanted at a surface 1010 of a subject for dehydration early inflammation detection. In the illustrated use example, the medical sensor 1000 is placed in a lacrimal punctum or a subconjunctival space of the subject. This allows the monitoring of analytes in the subject's tear, such as sodium, urea, and glucose for the dehydration, and interleukins and histamines for the early inflammation. Tear is readily availability and has reliable correlation to serum and low variance due to ambient conditions. It has a turnover around 12-16% per minutes, which correlates fast to serum changes. Moreover, the eye location has a number of unique practical advantages including ease of implanting and subsequent removal as well as possible interfacing to a sensor readout built into a glass-worn device (e.g., the light source 120, the light detector 130, and the computing system 140 of FIG. 1 are integrated to form the glass-worn device). Both locations lacrimal punctum and the subconjunctival space are minimally invasive and would result in nominal overlying tissue resulting in greatly enhancing the accuracy and sensitivity of the implanted sensor 1000.

The hydration status can be assessed by the osmolarity of serum calculated by Osmolarity=2×serum sodium (mEq/L)+body urea nitrogen (mg/dl)/2.8+glucose (mg/dl)/18. Hence, three serum analytes (e.g., sodium, urea and glucose) need to be measured for dehydration assessment. While saliva and urine are candidate fluids for analysis, the analytes in them are more readily influenced by, for examples, ambient temperature, oral artifacts and considerable day-to-day variance, and can be less practical. On the other hand, tear is body fluid that has a strong correlation to serum in terms of osmolarity. This has been demonstrated from subjects exposed to a period of hypertonic-hypovolemia and the subjects' osmolarities of tear and serum were compared. A strong correlation between tear and serum osmolarity exists (r=0.93), which is even larger than the correlation between urine specific gravity and serum osmolarity (r=0.72). This is consistent with the knowledge that sodium diffuses passively from the blood to the tear film and has excellent correlation with the plasma levels. Although the concentration of glucose in the tear film is approximately thirty times less than that in the serum, the daily variance of serum glucose is reflected quite accurately in tear. Finally, urea diffuses easily from blood into tear film so the urea content in tear is also correlated to that in serum at 97%. This is supported by the fact that measurement of urea concentration in tear, other than in serum, is used for the management of patients with renal disease. Therefore, tear is a good target fluid to detect dehydration by sodium, urea and glucose detection.

As illustrated, the medical sensor 1000 includes a body 1004, such as a punctual plug. The body 1004 includes a fluidic channel 1006 that allows the fluid of the subject, such as tear, to flow and reach an outer surface 1008 of the body 1004. The arrays 1002 of nanoscale tapered waveguides are securely attached to the outer surface 1008 in proximity to the fluidic channel 1006. For instance, biocompatible epoxy is used to bond the arrays 1002 to the outer surface 1008. In an example, the arrays 1002 are distributed around an opening of the fluidic channel 1006. On one hand, this circular distribution can ensure that the fluid enters the different nanoscale tapered waveguides. On the other hand, the circular distribution avoids the need to orient the outer surface 1008 in a particular orientation during the implantation of the medical sensor 1000. Instead, a subset of the arrays 1002 would be exposed to an external light source regardless of the orientation, thereby enabling the medical sensor 1000 to output a response light.

Although FIG. 10 illustrates an example implantation at an outer surface of an in vivo subject, a medical sensor described herein can be implanted inside a human or animal body or in other outer surfaces of the human or animal body. For example, the medical sensor can be implanted inside or surrounding a tissue or organ, inside a body cavity, inside the vascular system including artery, vein and lymphatic. In addition, the medical sensor can be implanted in an ex vivo transplanted organ or part of a transplanted organ or derived stem cell therapy.

Depending on the light source (e.g., the light emission rat), the light detector (e.g., sensing rate), and the computing system (e.g., processing rate), the medical sensor can support continuous and non-continuous measurements and data processing and non-continuous measurements and data processing.

In addition, different placements of the medical sensor are possible to measure different types of analytes according to different fields of medicine such as ophthalmology, neurology, endocrinology, gastroenterology, internal medicine, microbiology, allergy and immunology, andurology. In ophthalmology, the sensor is used to measure analytes in the lacrimal film, aqueous humor, and vitreous humor and can be implanted in the vitreous cavity, epi-retinal space, sub-retinal space, or in the suprachoroidal space. In another example, the medical sensor is used to measure analytes in the cerebrospinal liquid and can be implanted under the dura mater, pia mater, arachnoid mater or in direct contact with the brain. Also the medical sensor can be implanted in the lateral ventricles, third ventricle and fourth ventricle. In yet another example, the medical sensor is used to measure analytes for full clinical evaluation from the blood. The medical sensor can be placed at any central or periphery vein/arterial/lymphatic of the body. Also the medical sensor can be placed in the bone marrow of any bone. The fluid inside these structures is used for the measurements. In a further example, medical sensor is used to analytes from the urine and can be placed inside the bladder, ureters or urethra. The urine also can be measured from outside of the body using a handheld instrument. In another example, the medical sensor is used to measure analytes from the sweat and can be implanted in the surface of the body or installed in a handheld device for sweat-based measurements. In an additional example, the medical sensor is used to measure analytes from the saliva and can be placed inside the mouth in contact with the saliva or measured by a handheld device. In a further example, the medical sensor is used to measure analytes from the gastric juice and can be placed in the esophagus or stomach. In another example, the medical sensor is used to measure analytes from feces and can be placed in the jejunum, colon, or rectum. Also the medical sensor can measure the feces from outside the body using a handheld. In yet another example, the medical sensor is used to measure analytes from the bile juice and can be placed in the gall bladder or bile duct. In a further example, the medical sensor is used to measure analytes from the pancreatic juice and can be placed in the pancreas duct or duodenum. In an additional example, the medical sensor is used to measure analytes from the liquid of the joint and can be placed inside any joint of the human body. In another example, the medical sensor is used to measure analytes from the peritoneal fluids and can be placed in the peritoneal space or retroperitoneal.

Figure 11:
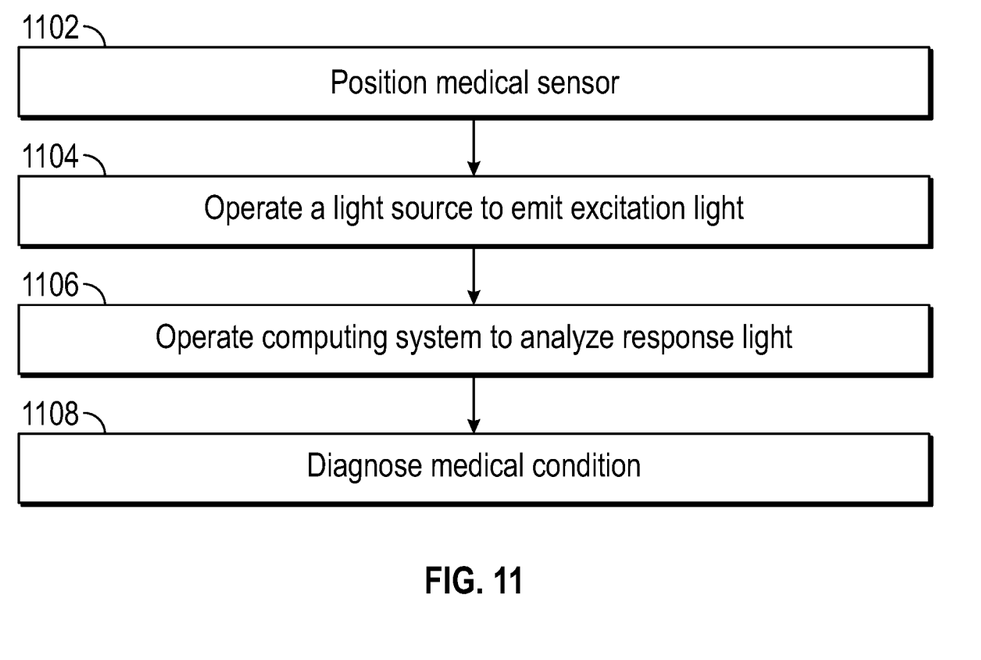
FIG. 11 illustrates an example flow for using a medical diagnosis system.

FIG. 11 illustrates an example flow for using a medical diagnosis system, similar to the system of FIG. 1. An operator operates the medical diagnosis system to perform the flow and diagnose a medical condition of a subject. In an example, the operator is a trained specialist that performs an in vivo, ex vivo, or in vitro diagnosis. In another example, the operator is the subject when the subject is human. In addition, the medical diagnosis system can be a distributed system, where the different components can interface with each other. Alternatively, the medical diagnosis system can be standalone device, such as a handheld device, that integrates some or all of the components.

The example flow starts at operation 1102, where a medical sensor is positioned. In an example, the operator implants a medical sensor in outer or inner surface of the subject. In another example, the medical sensor is placed in a laboratory equipment that includes fluid of the subject.

At operation 1104, the light source is operated to emit an excitation light. For example, the operator accesses an interface of the light source or of the computing system communicatively coupled to the light source to set various light emission parameters. In an example, the parameters include the frequency or frequencies of the excitation light, intensity, duration, transmission rate, and other light emission parameters. The excitation light is emitted from the light source towards the medical sensor according to the light emission parameters.

At operation 1106, the computing system is operated to analyze a response light. For example, the light detector receives the response light from the medical sensor. A response spectrum is generated from the response light. The operator accesses an interface to a medical application hosted on the computing system and configured to analyze the response spectrum according to a particular spectroscopy technique. The interface receives input of the operator to perform the analysis.

At operation 1108, a medical condition is diagnosed. For example, the medical application identifies the medical condition from the analysis and presents this medical condition at the interface. In another example, the operator analyzes the response spectrum to identify the medical condition.

In particular, observed values in the response spectrum are correlated to particular analytes in the fluid. These observed values and correlations identify the medical condition. In a further example, differential measurement technique can be used to calculate concentration of analytes. In this example, the medical sensor includes two sensor units. One unit outputs a light response from the fluid. The other unit is sealed (e.g., with a transparent permeable membrane) and includes a reference fluid. This unit outputs a reference light response. The differential measurement technique includes comparing the two responses, and other reference values previously recorded, to calculate the precise number of analytes in a unit volume.

Figure 12:
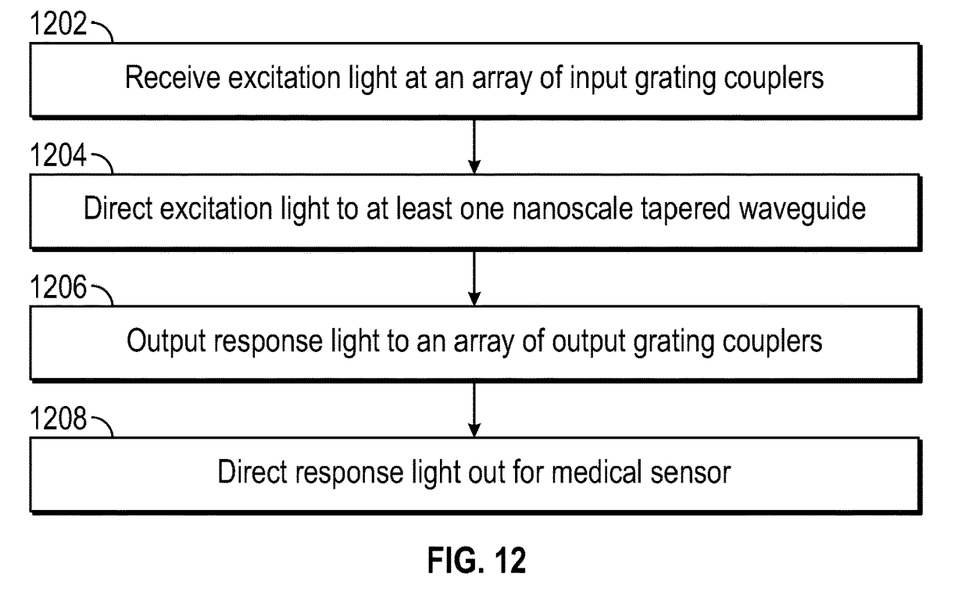
FIG. 12 illustrates an example flow for outputting a response light in response to an excitation light.

FIG. 12 illustrates an example flow for outputting a response light in response to an excitation light. The excitation light is emitted from a light source towards a medical sensor that includes an array of input grating couplers, at least one nanoscale tapered waveguide, and an array of output grating couplers as illustrated in FIGS. 6 and 7.

The example flow starts at operation 1202, where the excitation light is received at an array of input grating couplers. In an example, these couplers are attached to a substrate of the medical sensor. In a further example, the medical sensor includes a plurality of sensing portions contained in a bag, as illustrated in FIG. 7. In this example, the excitation light is received by a plurality of input grating couplers, each attached to a substrate of a sensing portion.

At operation 1204, the excitation light is directed to at least one nanoscale tapered waveguide. For example, the input grating couplers redirect the excitation light towards to the at least one nanoscale tapered waveguide. In an example, an array of such waveguides is disposed on the same substrate as the array of input grating couplers, similarly to the arrangement of FIG. 6. In this example, the excitation light is directed to some or all of the nanoscale tapered waveguides. In another example, a single nanoscale tapered waveguide is attached to the substrate and belong to a sensing portion of the medical sensor, similarly to the arrangement of FIG. 7. In this example, the excitation light is directed from the array of input grating couplers to the single nanoscale tapered waveguide. In both examples, a nanoscale channel of the at least one nanoscale tapered waveguide receives the excitation light. The nanoscale channel also includes fluid.

At operation 1206, the response light is outputted to an array of output grating couplers. This array is disposed on the same substrate as the array of input grating couplers and the at least one nanoscale tapered waveguide. In particular, the at least one nanoscale tapered waveguide is located between the two arrays. The response light is outputted from the nanoscale channel of the at least one nanoscale tapered waveguide towards the array of output grating couplers and corresponds to a response of analytes of fluid present in an optical response channel of the nanoscale channel.

At operation 1208, the response light is directed out from the medical sensor. For example, the array of output grating couplers direct the response light towards a light detector.

Figure 13:
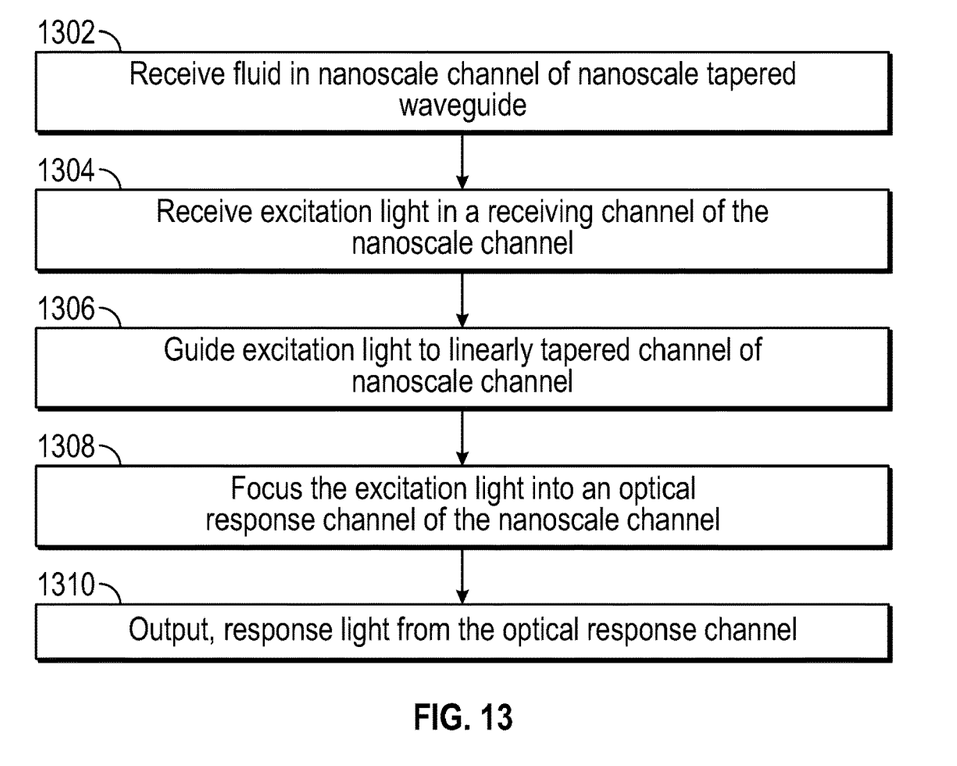
FIG. 13 illustrates an example flow for outputting a response light from a nanoscale tapered waveguide in response to an excitation light.

FIG. 13 illustrates an example flow for outputting a response light from a nanoscale tapered waveguide in response to an excitation light. The excitation light is emitted towards a nanoscale channel of the nanoscale tapered waveguide. The nanoscale channel represents a fluidic and optical channel having a nanoscale size and includes a receiving channel, a linearly tapered channel, and an optical response channel.

The example flow starts at operation 1302, where fluid is received in the nanoscale channel. The fluid can belong to a subject. The excitation light and response light facilitate spectroscopy-based analysis of analytes in the fluid to diagnose a medical condition of the subject. In an example, the fluid fills up the receiving channel, linearly tapered channel, and optical response channel.

At operation 1304, the excitation light is received in the receiving channel of the nanoscale channel. In an example, the excitation light is directed from a grating coupler to the receiving channel.

At operation 1306, the excitation light is guided to the linearly tapered channel. For example, the excitation light propagates through the fluid present in the receiving channel, where the receiving channel acts as a waveguide. The linearly tapered channel is connected to the receiving channel and receives the guided excitation light from the receiving channel.

At operation 1308, the excitation light is focused into the optical response channel. For example, the linearly tapered channel has 3D linear tapering directed from the receiving channel towards the optical response channel. Accordingly, the excitation light propagates through the fluid present in the linearly tapered channel, where the 3D linear tapering focuses the excitation light into the optical response channel.

At operation 1310, the response light is outputted from the optical response channel. For example, the fluid present in the optical response channel contains analytes. One or more properties (e.g., molecular vibration, molecular rotation, electronic state) of one or more of such analytes change in response to the excitation light that is focused from the linearly tapered channel. The response light is emitted based on this change. The optical response channel acts as a waveguide to guide the response light outwards from the nanoscale tapered waveguide.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain. "About" includes within a tolerance of ±0.01%, ±0.1%, ±1%, ±2%, ±3%, ±4%, ±5%, ±8%, ±10%, ±15%, ±20%, ±25%, or as otherwise known in the art. "Substantially" refers to more than 66%, 75%, 80%, 90%, 95%, or, depending on the context within which the term substantially appears, value otherwise as known in the art.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A medical sensor, comprising:
   a substrate; and
   a nanoscale tapered waveguide attached to the substrate and comprising:
     a first rail comprising a first bottom edge and a first top edge, wherein the first bottom edge is attached to the substrate, and wherein the first bottom edge and the first top edge define a variable height of the first rail;
     a second rail spaced apart from the first rail and comprising a second bottom edge and a second top edge, wherein the second bottom edge is attached to the substrate, wherein the first top edge of the first rail and the second top edge of the second rail define an opening between the first rail and the second rail, and wherein the first rail and the second rail define corresponding walls of a receiving channel of the nanoscale tapered waveguide;
     the receiving channel having a height within a range of 250 nm to 750 nm and a width within a range of 150 nm to 250 nm, the receiving channel comprising the opening and formed by at least a first portion of the first rail and a first portion of the second rail, the first portions substantially parallel to each other, the receiving channel configured to receive fluid and guide an excitation light;
     a linearly tapered channel configured to receive the fluid and focus the excitation light guided from the receiving channel, the linearly tapered channel formed by at least a second portion of the first rail and a second portion of the second rail, the second portions linearly tapered relative to each other along two axes; and
     an optical response channel configured to receive the fluid and to output a response light to the excitation light focused from the linearly tapered channel, the optical response channel formed by at least a third portion of the first rail and a third portion of the second rail, the third portions substantially parallel to each other, the optical response channel having a height within a range of 40 nm to 120 nm and a width within a range of 10 nm to 20 nm, the response light based on a response of an analyte of the fluid to the excitation light focused from the linearly tapered channel.

2. The medical sensor of claim 1, further comprising an input blazed grating coupler attached to the substrate and configured to direct the least one excitation light from a light source into the receiving channel.

3. The medical sensor of claim 2, wherein the input grating coupler has a Littrow configuration.

4. The medical sensor of claim 1, further comprising an output grating coupler attached to the substrate and configured to direct the response light from the response channel to a light detector.

5. The medical sensor of claim 1, further comprising a plurality of nanoscale tapered waveguides attached to the substrate, a plurality of input grating couplers attached to the substrate, and a plurality of output grating couplers attached to the substrate, wherein the plurality of nanoscale tapered waveguides are disposed between the plurality of input grating couplers and the plurality of output grating couplers.

6. The medical sensor of claim 5, wherein the plurality of input grating couplers are substantially parallel to the plurality of output grating couplers and are substantially perpendicular to the plurality of nanoscale tapered waveguides.

7. The medical sensor of claim 1, further comprising input grating couplers attached to the substrate and output grating couplers attached to the substrate, wherein the substrate, the nanoscale waveguide, the input grating couplers, and the output grating couplers form a sensing portion of the medical sensor, and wherein the medical sensor comprises a plurality of sensing portions, each of the sensing portions comprising respective substrate, nanoscale waveguide, input grating couplers, and output grating couplers.

8. The medical sensor of claim 7, further comprises a bag that contains the plurality of sensing portions, wherein the plurality of sensing portions have random orientations inside the bag.

9. The medical sensor of claim 1, further comprising input grating couplers attached to the substrate, output grating couplers attached to the substrate, and a semi-permeable membrane that forms a bag around the substrate, the nanoscale waveguide, the input grating couplers, and the output grating couplers.

10. The medical sensor of claim 9, wherein the semi-permeable membrane comprises parylene-C material.

11. The medical sensor of claim 10, wherein the thickness of the parylene-C material is in the range of 0.5 µm to 1.5 µm.

12. The medical sensor of claim 1, wherein the substrate and the nanoscale tapered waveguide are made of biocompatible materials.

13. The medical sensor of claim 12, wherein the substrate is made of silicone dioxide, and wherein the rails of the tapered waveguide are made of gold.

14. The medical sensor of claim 1, wherein the analyte comprises a molecule, wherein the response light corresponds to resonance of a molecular vibration of the molecule and has a peak frequency that is different than a peak frequency of the excitation light.

15. The medical sensor of claim 1, wherein the receiving channel has a length within a range of 1 μm to 2 μm.

16. The medical sensor of claim 1, wherein the linearly tapered channel has a lateral tapering angle within a range of 20° to 40° and a vertical tapering angle within a range of 20° to 30°.

17. The medical sensor of claim 1, wherein one end of the linearly tapered channel has a first height and a first width, where the first height is within a range of 250 nm to 750 nm and corresponds to the height of the receiving channel, wherein the first width is within a range of 150 nm to 250 nm and corresponds to the width of the receiving channel, and wherein an opposite end of the linearly tapered channel has a second height and a second width, wherein the second height is within a range of 40 nm to 120 nm and corresponds to the height of the optical response channel, and wherein the second width is within a range of 10 nm to 20 nm and corresponds to the width of the optical response channel.

18. The medical sensor of claim 1, wherein the optical response channel has a length within a range of 150 to 250 nm.

19. The medical sensor of claim 1, further comprising an array of grating couplers attached to the substrate, wherein the array has a length within a range of 600 μm to 1600 μm and a width within a range of 50 μm to 150 μm.

20. The medical sensor of claim 1, further comprising a punctal plug, and wherein one surface of the substrate is attached to the punctal plug and an opposite surface of the substrate is attached to the nanoscale tapered waveguide.

21. The medical sensor of claim 1, wherein the excitation light comprises a plurality of laser beams at different frequencies, and wherein the response light enables coherent anti-Stokes Raman spectroscopy (CARS).

22. The medical sensor of claim 1, wherein the excitation light comprises a laser beam, and wherein the response light enables Raman spectroscopy.

23. The medical sensor of claim 1, wherein the excitation light comprises a fluorescent light, and wherein the response light enables fluorescence spectroscopy.

* * * * *